(12) United States Patent
Brewer et al.

(10) Patent No.: US 7,691,994 B2
(45) Date of Patent: Apr. 6, 2010

(54) COMPOSITIONS AND METHODS FOR THE DETECTION OF HUMAN T CELL RECEPTOR VARIABLE FAMILY GENE EXPRESSION

(76) Inventors: Jamie L. Brewer, Rt. 1, Box 258T, Clarksburg, WV (US) 26301-9741; Solveig G. Ericson, 829 Briarwood St., Morgantown, WV (US) 26505

( * ) Notice: Subject to any disclaimer, the term of this patent is extended or adjusted under 35 U.S.C. 154(b) by 711 days.

(21) Appl. No.: 10/612,121

(22) Filed: Jul. 2, 2003

(65) Prior Publication Data

US 2004/0014127 A1    Jan. 22, 2004

Related U.S. Application Data

(60) Provisional application No. 60/393,995, filed on Jul. 3, 2002.

(51) Int. Cl.
*C07H 21/04* (2006.01)
(52) U.S. Cl. .................................. 536/24.33; 435/810
(58) Field of Classification Search ....................... None
See application file for complete search history.

(56) References Cited

U.S. PATENT DOCUMENTS 6,017,699 A  *  1/2000  Jordan ........................... 435/6

OTHER PUBLICATIONS

Wei et al., 1994, Human Immunology, vol. 41: 201-206.*
Kwok et al. 1994, PCR methods Appl. vol. 3:39-47.*
Genevee, C., et al., "An experimentally validated panel of subfamily-specific oligonucleotide primers (V alpha 1-w29/V beta 1-w24) for the study of human T cell receptor variable V gene segment usage by polymerase chain reaction", Dur. J. Immunol., May 1992, vol. 22, pp. 1261-1269.

Roman-Roman, S., et al., Studies on the human T cell receptor alpha/beta variable region genes, I. Identification of seven additional V apha subfamilies and fourteen J alpha gene segments. Eur. J. Immunol., Apr. 1991, vol. 21, pp. 927-933.

Spinella, D.G., et al., "Analysis of Human T-Cell Repertoires by PCR." in The Polymerase Chain Reaction, (Birkhauser, Mullis, K.B., ed.), 1994, pp. 110-120.

* cited by examiner

*Primary Examiner*—Amy E Juedes
(74) *Attorney, Agent, or Firm*—Steptoe & Johnson PLLC

(57) ABSTRACT

Compositions and methods for the assessment of T cell receptor variable subunits. The present invention provides nucleotide sequences for the evaluation of the expression of TCRV families. These nucleotides sequences were obtained through a bioinformatic investigation of the nucleotide sequences for TCRVα and TCRVβ families. The nucleotide sequences of the present invention uniquely recognize each and every subfamily and allelic member of a particular TCRV family, while at the same time not recognizing the members of any other TCRV family. This unique expression recognition profile of the nucleotide sequences of the present invention provides great utility for the assessment of TCR families in a clinical setting, such as through polymerase chain reactions, gene chip technology, and direct electrophoretic measurement of DNA or RNA.

2 Claims, 3 Drawing Sheets

US 7,691,994 B2

COMPOSITIONS AND METHODS FOR THE DETECTION OF HUMAN T CELL RECEPTOR VARIABLE FAMILY GENE EXPRESSION

CROSS REFERENCE TO RELATED APPLICATIONS

This application claims priority to U.S. Provisional Application No. 60/393,995 filed Jul. 3, 2002.

The disclosed invention was made with government support under award No. RR164402 from the National Institute of Health. The government has certain rights in this invention.

BACKGROUND OF THE INVENTION

1. Field of the Invention

The present invention relates to novel compositions and sequences useful for the evaluation of T cell receptor genes and their expression, and therapeutic applications thereof.

2. Description of the Background

T cells constitute a cellular component of the immune system that is able to identify and target foreign antigens for destruction by the immune system. At the same time, T cells must be able to identify cells from the host organism, so that the immune system does not attack the body itself. T cells interact with antigens and the body through receptors (T cell receptors; TCR) located on the T cell surface.

TCRs are heterodimers having an alpha ($\alpha$) and a beta ($\beta$) subunit, each of which include variable (V) and constant (C) regions. It is the variable region of these chains that directly contacts the major histocompatibility (a:MHC) complex located on the surface of all cells, thereby eliciting the T cell response. Each individual has multiple TCRV($\alpha$) and TCRV($\beta$) gene segments, providing for the ability to respond to a large number of a:MHCs.

Prior to 1995, there was no uniform or systematic organization of the genetic sequences that code for the TCRV$\alpha$ and TCRV$\beta$ families. An international group was created to address this problem, and, as a result, Arden, Clark, Kabelitz, and Mak (Immunogenetics 42, 455; 1995, which is hereby incorporated by reference) applied a consistent classification scheme to all known human TCRV$\alpha$ and TCRV$\beta$ gene families. Based on this classification system, there are 32 different functional variable $\alpha$ families with 69 subfamily members and 25 different functional variable $\beta$ families with 91 subfamily members. According to the proposed nomenclature, TCRs are named according to the following convention, receptor subunit; family; subfamily; allele. Thus, AV1S2A3 refers to the T cell receptor $\alpha$ variable receptor, family 1, subfamily 2, and allele 3. This naming convention will be used herein.

It is of great clinical and scientific interest to evaluate the expression of TCR families accurately in individual patients, as this repertoire is a reflection of the immune response in those patients. One possible way to analyze the expression of T cell receptors could be through the use of antibody-based analysis of the surface receptor protein. However, a comprehensive evaluation is not currently possible due to the lack of antibodies to all of the different members of human TCR variable $\alpha$ and $\beta$ families.

An alternative approach is to analyze gene expression of the TCRV$\alpha$ and TCRV$\beta$ regions. Previous attempts at establishing methods to evaluate the expression of all members of the TCR families have not taken into account the new systematic classification of Arden et al. or the wide variety of subfamilies and alleles that exist for many of the variable families. Accordingly, nucleotide probes that have been previously published in the literature do not consistently recognize all subfamily members of a particular TCR family. For example, a nucleotide probe may only recognize AV2S1A1 and not the other alleles and subfamily members of the AV2 family. Therefore, no broad statements regarding the expression of the AV2 family may be made using this probe. Given the large degree of diversity among TCRs, the inadequacy of presently-available nucleotide probes dramatically reduces their clinical and experimental utility.

Thus, there has been a long-standing need in the molecular biological and clinical communities for a genetic tool that can be used to evaluate specifically the expression of the T cell surface receptors in a patient. The genetic tool should be able to identify each family of $\alpha$ and $\beta$ TCRs independently, while, at the same time, recognizing all subfamily members and alleles within that family. Such a collection of nucleotide probes would significantly advance the state of the art and the ability of clinicians to evaluate the repertoire of T cells in the body.

SUMMARY OF THE INVENTION

The present invention, in accordance with at least one presently-preferred embodiment, generally contemplates nucleotide sequences that specifically identify all subfamily and allelic members of a TCRV family. SEQ ID Nos: 1 through 32 provide for the specific identification of the various families of TCRV$\alpha$ receptor cDNA, mRNA, and genomic DNA. SEQ ID Nos: 33 through 55 provide for the specific identification of the various families of TCRV$\beta$ receptor cDNA, mRNA, and genomic DNA. Unlike prior art nucleotide primers, the nucleotide primers of the present invention identify all members of the TCRV families. The terms 'nucleotide probe' and 'nucleotide primer' are used to describe nucleotide sequences that may or may not, depending upon the application, include a marker, such as a fluorescent, chemiluminescent, or radioactive marker.

Also considered within the scope of the present invention are nucleotide sequences that differ from SEQ ID Nos: 1 through 55 that differ by up to eight nucleotides, but more often by one or two nucleotides. Also included within the scope of the present invention are nucleotide sequences that are the complementary nucleotide sequences of SEQ ID Nos: 1 through 55.

The nucleotide sequences of the present invention may be used in an expression system to obtain multiple copies of the nucleotide sequences, to produce unique peptides that correspond to specific families of TCRV receptors, or for the production of monoclonal antibodies. In addition, use of the nucleotide sequences of the present invention in sequencing TCRV receptors is also contemplated. The techniques employed to perform these tasks are commonly known to those of skill in the art.

In an embodiment of the present invention, at least one of SEQ ID Nos: 1 through 55 are inserted into a plasmid vector. The plasmid vector may include control elements, such as a promoter, a repressor, or an enhancer designed to help control the expression of SEQ ID Nos: 1 through 55. The plasmid may then be transfected into an expression system, such as a bacterial host or a mammalian cell line. The expression system may be useful, for example, in the production of peptides for use in the generation of antibodies to the families of TCRV families.

The nucleotide sequences provided by the present invention can be used by the research community for various purposes. The nucleotide sequences can be used to express recombinant protein for analysis, characterization or therapeutic use; as chromosome markers or tags (when labeled) to identify chromosomes or to map related gene positions; to compare with endogenous DNA sequences in patients to identify potential genetic disorders; as probes to hybridize and thus discover novel, related DNA sequences; as a source of information to derive PCR primers for genetic fingerprinting; as a probe to "subtract-out" known sequences in the process of discovering other novel nucleotide sequences; for selecting and making oligomers for attachment to a "gene chip" or other support, including for examination of expression patterns; to raise anti-protein antibodies using DNA immunization techniques; and as an antigen to raise anti-DNA antibodies or elicit another immune response. Where the nucleotide sequences encode a protein which binds or potentially binds to another protein (such as, for example, in a receptor-ligand interaction), the nucleotide sequences can also be used in interaction trap assays (such as, for example, that described in Gyuris et al., Cell 75:791-803 (1993)) to identify nucleotide sequences encoding the other protein with which binding occurs or to identify inhibitors of the binding interaction.

A further aspect of the present invention is the use of the nucleotide sequences of the present invention in gene chips. All or a subset of SEQ ID Nos: 1 through 32 may be used to assess the expression of mRNA and/or cDNA for TCRVα. All or a subset of SEQ ID Nos: 33 through 55 may be used to assess the expression of mRNA and/or cDNA for TCRVβ. The nucleotide sequences, or their complement, may be attached to a fixed medium and samples including mRNA or cDNA that has been extracted or generated from a sample of T cells may be exposed to the fixed medium to assess the expression of TCRV.

Another aspect of the present invention is a kit for assessing the expression of Vα TCR in a patient, said kit comprising SEQ ID Nos: 1 through 32, an enzyme capable of performing a polymerase chain reaction, deoxynucleotide phosphates, and appropriate buffers. The use of the sequences of the present invention may also include microplate hybridization assays and, more specifically, enzyme-linked immunosorbent assays (ELISA).

A still further aspect of the present invention is a kit for assessing the expression of Vβ TCR in a patient, said kit comprising SEQ ID Nos: 33 through 55, an enzyme capable of performing a polymerase chain reaction, deoxynucleotide triphosphates and appropriate buffers.

BRIEF DESCRIPTION OF THE DRAWINGS

The present invention and its presently preferred embodiments will be better understood by reference to the detailed disclosure hereinbelow and to the accompanying drawings, wherein.

DETAILED DESCRIPTION OF THE PREFERRED EMBODIMENTS OF THE PRESENT INVENTION

Figure 1:
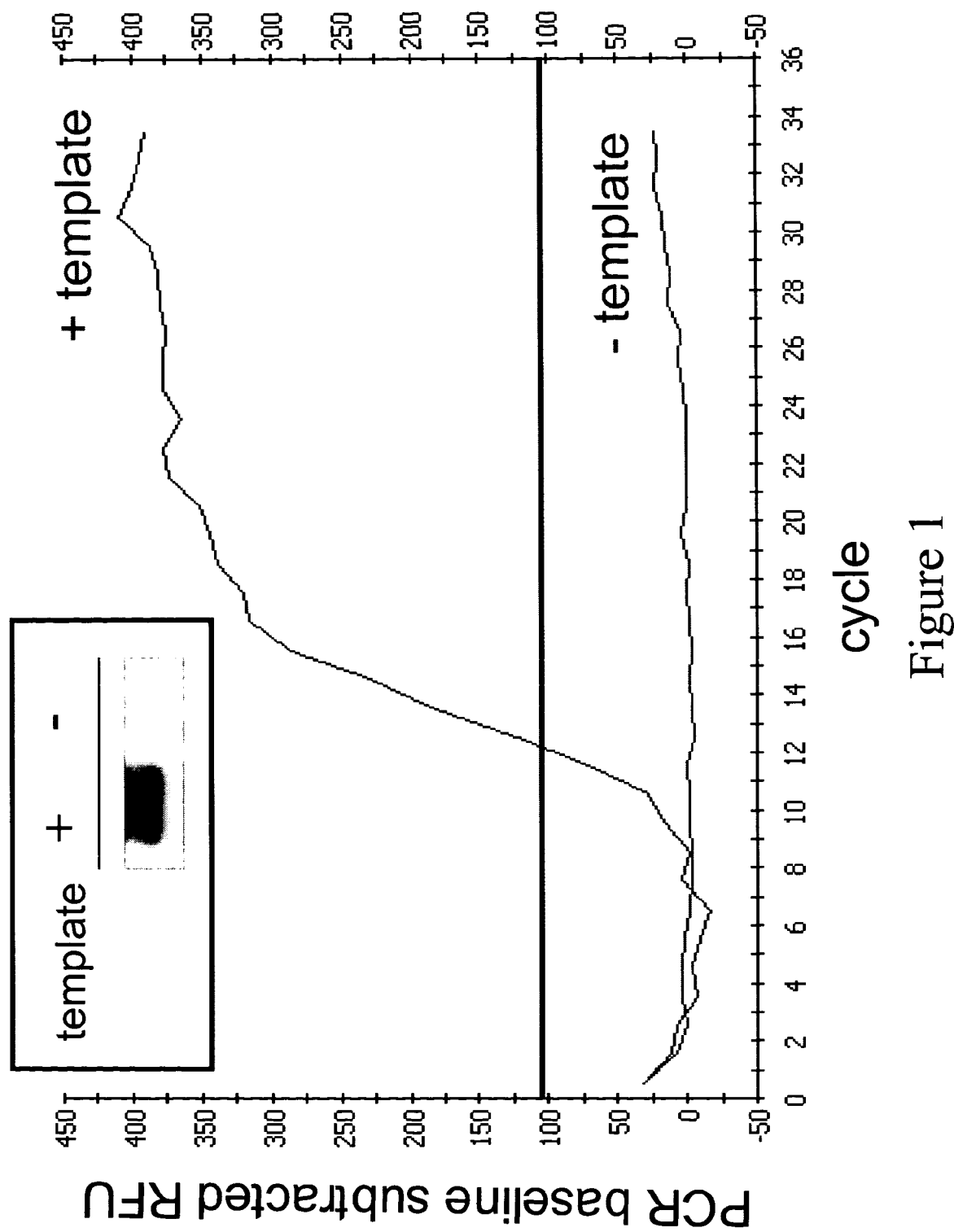
FIG. 1 displays the progression of a real time polymerase chain reaction.

The present invention provides nucleotide sequences for the evaluation of the expression of TCRV families. The nucleotide sequences of the present invention uniquely recognize each and every subfamily and allelic member of a particular TCRV family, while at the same time not recognizing the members of any other TCRV family. In other words, the nucleotide sequences of the present invention uniquely identify all members of a family of TCRs, irrespective of the subfamily or allele. Further, the present invention provides nucleotide sequences for each and every α and β TCRV family identified by Arden et al. (1995). This unique expression recognition profile of the nucleotide sequences of the present invention provides great utility for the assessment of TCRV families in a clinical or basic research setting.

In order to determine nucleotide sequences of the present invention, a bioinformatic approach was employed. The sequence information for each subfamily and allelic member of a TCRV family was obtained from Genbank (National Center for Biotechnology Information) and was evaluated for similarities in sequence. Sequences that were common to each subfamily and allelic member were identified by direct evaluation of the published sequences. The ability of these sequences to identify other TCRV families was evaluated using a nucleotide sequence analysis program such as BLAST. The sequences displayed in Tables 1 and 2 represent the outcome of that analysis. Each sequence listed in Table 1 uniquely identifies all members of the indicated Vα receptor family. In some cases, the primer had been previously reported by Hercend et al. as indicated. However, many of the sequences that are listed in Table 1 have been identified by the present inventors.

TABLE 1

| TCRVα family | Sequence | SEQ ID NO | Ref. |
|---|---|---|---|
| A1 | GGCATTAACGGTTTTGAGGCTGGA | 1 | * |
| A2 | TCAGTGTTCCAGAGGGAGCCA | 2 | |
| A3 | CCGGGCAGCAGACACTGCTTCTTA | 3 | * |
| A4 | TTGGTATCGACAGCTTCACTCCCA | 4 | * |
| A5 | CGGCCACCCTGACCTGCAACTATA | 5 | * |
| A6 | TCCGCCAACCTTGTCATCTCCGCT | 6 | * |
| A7 | GCAACATGCTGGCGGAGCACCCAC | 7 | * |
| A8 | CCTGAGTGTCCAGGAGGGAGAC | 8 | |
| A9 | CCAGTACTCCAGACAACGCCTGCA | 9 | * |
| A10 | GGACAGTTCTCTCCACATCACTGC | 10 | |
| A11 | GCTGCTCATCCTCCAGGTGGG | 11 | |
| A12 | TCGTCGGAACTCTTTTGATGAGCA | 12 | * |
| A13 | TTCATCAAAACCCTTGGGGACAGC | 13 | * |
| A14 | CCCAGCAGGCAGATGATTCTCGTT | 14 | * |
| A15 | TTGCAGACACCGAGACTGGGGACT | 15 | * |
| A16 | TCAACGTTGCTGAAGGGAATCCTC | 16 | * |
| A17 | TGGGAAAGGCCGTGCATTATTGAT | 17 | * |
| A18 | CAGCACCAATTTCACCTGCAGCTT | 18 | * |
| A19 | ACACTGGCTGCAACAGCATCCAGG | 19 | * |
| A20 | TCCCTGTTTATCCCTGCCGACAGA | 20 | * |
| A21 | AGCAAAATTCACCATCCCTGAGCG | 21 | * |

TABLE 1-continued

| TCRVα family | Sequence | SEQ ID NO | Ref. |
|---|---|---|---|
| A22 | CCTGAAAGCCACGAAGGCTGATGA | 22 | * |
| A23 | TGCCTCGCTGGATAAATCATCAGG | 23 | * |
| A24 | CTGGATGCAGACACAAAGCAGAGC | 24 | * |
| A25 | TGGCTACGGTACAAGCCGGACCCT | 25 | * |
| A26 | AGCGCAGCCATGCAGGCATGTACC | 26 | * |
| A27 | AAGCCCGTCTCAGCACCCTCCACA | 27 | * |
| A28 | TGGTTGTGCACGAGCGAGACACTG | 28 | * |
| A29 | CCTGATGATATTACTGAAGGGTGG | 29 | |
| A30 | CTTCACCCTGTATTCAGCTGGGG | 30 | |
| A31 | GGGGTACCCTACCCTTTTCTGG | 31 | |
| A32 | CCAGCATGTACAAGAAGGAGAGG | 32 | |

* These primers were defined in Genevee-Gaudin, et al., Eur. J. Imunol. 1992 22:1261-1269. The listings for which no reference is entered have been uniquely identified as recognizing every member of that TCRV family.

The nucleotide sequences displayed in Table 1 provides primers for the evaluation of the expression of Vα TCRs. These primers may be used in polymerase chain reactions (PCR), as described hereinbelow, to assess the expression of Vα TCRs rapidly.

Table 2 displays the results of the same analysis for Vβ receptor family. Some numbered families of TCRVβ receptors do not express functional surface receptors. Those families are omitted from the analysis presented herein.

TABLE 2

| TCRVα family | Sequence | SEQ ID No: | Ref. |
|---|---|---|---|
| B1 | CCGCACAACAGTTCCCTGACTTGC | 33 | † |
| B2 | GGCCACATACGAGCAAGGCGTC | 34 | ‡ |
| B3 | CGCTTCTCCCGGATTCTGGAGTCC | 35 | † |
| B4 | TTCCCATCAGCCGCCCAAACCTAA | 36 | † |
| B5 | TGTGTCCTGGTACCAACAG | 37 | |
| B6 | CAGCGCACAGAGCAGGGG | 38 | |
| B7 | CCTGAATGCCCCAACAGCTCTC | 39 | |
| B8 | GGTACAGACAGACCATGATGC | 40 | |
| B9 | TTCCCTGGAGCTTGGTGACTCTGC | 41 | † |
| B11 | TGCCAGGCCCTCACATACCTCTCA | 42 | † |
| B12.1 | TGTCACCAGACTGAGAACCACC | 43 | |
| B13.1 | CTGCAGTGTGCCCAGGATATGAACC | 44 | |
| B14 | GAGTCGCCCAGCCCCAAC | 45 | |
| B15 | CAGGCACAGGCTAAATTCTCCCTG | 46 | † |
| B16 | GCCTGCAGAACTGGAGGATTCTGG | 47 | † |

TABLE 2-continued

| TCRVα family | Sequence | SEQ ID No: | Ref. |
|---|---|---|---|
| B17 | GAAAGGAGATATAGCTGAAGGGTAC | 48 | ‡ |
| B18 | GATGAGTCAGGAATGCCAAAGG | 49 | |
| B20 | CTGGCTTCTATCTCTGTGCCTGG | 50 | |
| B21 | CCACTCTCAAGATCCAGCCTGC | 51 | |
| B22 | AAGTGATCTTGCGCTGTGTCCCCA | 52 | † |
| B23 | CAGGGTCCAGGTCAGGAC | 53 | |
| B24 | CCCAGTTTGGAAAGCCAGTGACCC | 54 | † |
| B25 | GAAACAGGTATGCCCAAGGAAAG | 55 | |

† These primers were defined in Genevee-Gaudin, et al., Eur. J. Imunol. 1992 22:1261-1269;
‡ These primers were defined in Blumberg, et al., J. Immunol. 1993 150 (11):5144-5153.
The listings for which no reference is entered have been uniquely identified as recognizing every member of that TCRV family.

The nucleotide sequences displayed in Table 2 provides primers for the evaluation of the expression of Vβ TCRs. These primers may be used in PCR, as described hereinbelow, to assess the expression of Vβ TCRs rapidly.

The following sequence (SEQ ID No: 58) is common to all TCRVα: CCAGATGTGTAAGGCTGTGGATC.

The following sequence (SEQ ID No: 59) is common to all TCRVβ: GCTGCTCCTTGAGGGGCTGC.

Below an example of the use of the nucleotide sequences of the present invention for analysis of TCRVβs from human blood will be presented. The specific conditions of the reactions, the concentration of the reagents used, and the specific techniques that are employed to measure data in the experiments described hereinbelow are meant to be illustrative. One of skill in the art would recognize multiple variations on the described experimental approach. Parallel experiments for TCRVαs are contemplated as being within the scope of the present invention.

EXAMPLE

A volume of approximately 20 milliliters of peripheral blood was collected via venipuncture from individual healthy donors into an acid citrate dextrose vacutainer blood collection tube (Becton Dickinson). White blood cells were isolated via centrifugation at 3300 rcf for 10 minutes. Contaminating red blood cells were removed by hypotonic lysis. By staining for select lymphocyte markers, it was determined that approximately 50-60% of the cells were CD4+ T cells, approximately 25% CD8+ T cells, and 2-5% CD19+ B cells.

Total RNA was isolated from 20-40×10$^6$ white blood cells using Trizol Reagent through techniques commonly-known to one of skill in the art (AMBION). RNA was dissolved in ultra-pure, DNAse- and RNAse-free water. Dnase treatment was performed on isolated RNA according to techniques commonly-known to one of skill in the art. RNA purity and concentration was determined by standard 260 nm:280 nm spectrophotometric analysis using a Genesis 10 UV Spectronic Unicam (Spectronic Instruments).

One step reverse transcriptase-polymerase chain reaction was performed using the QuantiTect Probe RT-PCR kit (QIAGEN). Specifically, real time PCR was employed. While this technique is particularly useful for rapid analysis of TCR expression, standard PCR practice may also be employed. A fluorescent nucleotide probe was used to monitor the progression of the PCR reaction. In order to be useful as a generalized probe, the fluorescent probe should recognize all members of the α or β families. Accordingly, a fluorescent nucleotide primer was designed by identifying a sequence that is common to all members of TCRVα, being TCRCA, and another fluorescent nucleotide primer was designed by identifying a sequence that is common to all members of TCRVβ, being TCRCB. On the 5' end of the primer, a fluorescent molecule (6-FAM) was attached. On the 3' end of the primer, a fluorescence quencher was attached (BHQ-1). When the primer is intact, the quencher absorbs all of the fluorescence of the fluorescent dye. However, if the molecule is broken apart or degraded, e.g. by nick translation during replication of a nucleotide, the quencher and dye are no longer in proximity to one another and the dye releases measurable fluorescence. In this way, the progression of the PCR reaction may be assessed directly in the reaction tube. The nucleotide probe for the TCRα (TCRCA) and for the TCRβ (TCRCB) subunits may be found in Table 3.

skilled in the art. cDNA purity and concentration was determined by standard 260 nm:280 nm spectrophotometric analysis using a Genesis 10 UV spectronic Unicam (Spectronic Instruments). cDNA dilutions were performed using ultra-pure distilled DNAse and RNAse free water (Invitrogen).

Nucleic acid bands were transferred from the 2% agarose gel to BioBond Plus Nylon Membrane (Sigma Chemical Co.) using the Alkaline Southern Breeze Blotting Kit (Sigma Chemical Co.). The membrane was blocked overnight at room temperature using a blocking solution of 1× saline-sodium citrate (SSC), 1% bovine serum albumin (BSA), and 1% sodium dodecyl sulfate (SDS). A one hour incubation at room temperature was then performed using 20 picomoles of biotinylated primary probe per ml of blocking buffer followed by three five-minute washings with a wash buffer of 1×SSC and 1% SDS. A streptavidin-HRP conjugate was added at a 1:5000 dilution in blocking buffer for 1 hour at room temperature. Three final five-minute washes were performed using the wash buffer. The membrane was developed using ECL detection reagents (Amersham Biosciences). The membrane was then exposed to film which was subsequently developed.

TABLE 3

| Probe Name | Sequence | SEQ ID No: |
|---|---|---|
| TCRCA | (5' 6-FAM) CCTACCGATCCTGCTCCTCCTGGCACAGGATC (3' BHQ-1) | 56 |
| TCRCB | (5' 6-FAM) TCTGTGCTGACCCCACTGTGCACCTCCTTCCC (3' BHQ-1) | 57 |

Recommended PCR reaction mixtures were scaled down to a total reaction volume of 20 μl using 0.04 μg RNA with the following primer and probe concentrations: 0.4 μM TCRV primer (Biosource International), 0.4 μM TCRC primer (Biosource International), and 0.2 μM TCRC TaqMan probe, 5' 6-FAM, 3' BHQ-1 (Integrated DNA Technologies, Inc.). 18SrRNA control reactions were performed in parallel using 0.4 μM each of sense and anti-sense primers (Biosource International) with 0.2 μM 18SrRNA TaqMan probe, 5' 6-FAM, 3' BHQ-1 (Integrated DNA Technologies, Inc.). An iCycler (BioRad Laboratories) was used for the assessment of fluorescence, i.e. reaction progression.

Reactions were performed at 50° C. for 60 minutes at the maximal ramp speed, followed by an initial *T. aquaticus* DNA polymerase I activation step of 15 minutes at 95° C. at the maximal ramp speed. A TouchDown PCR approach (Don et al., 1991) was used with the following cycling conditions: denaturation for 15 seconds at 95° C., max ramp speed, annealing for 30 seconds starting at 70° C. decreasing by 2° C. for 10 repeats, min ramp speed, and extension for 40 seconds at 72° C., max ramp speed. After this step down of the annealing temperature, 40 cycles of PCR were performed as follows: 15 seconds at 95° C., 30 seconds at 52° C., and 40 seconds at 60° C. Reactions were held at 4° C. upon the conclusion of the run. The exact cycling conditions described herein are used for illustrative purposes only. Fluorescent measurements were performed at each extension step. Amplification efficiencies using cDNA dilutions were determined using the described step-down cycling protocol with the deletion of the reverse transcription cycle of 50° C. for 60 minutes.

PCR products were electrophoresed on a 2% agarose gel using 20 μl PCR product and 4 μl tri-color 6× loading dye (Promega). Promega PCR marker was loaded into a control lane per the manufacturer's specification (Promega). Product bands were excised using the QIAquick gel extraction kit protocol according to protocols commonly known to one All flow cytometric analysis was performed using a FAC-Scan (Becton Dickinson), which had been calibrated using three color Calibrite beads and FACSCOMP software. For further lymphocyte analysis, 10,000 observations were collected for each sample. A total of 5,000 CD3+ cells were collected for analysis of each IOTest TCR Vβ expression sample. Side scatter and front scatter data were acquired in the linear mode and the FL1, FL2, and FL3 parameters were collected logarithmically.

FIG. 1 displays the results from a control experiment performed with the TCRCB probe (Table 3) using cDNA extracted from a previously-run RT-PCR reaction using RNA from human white blood cells. The abscissa represents the cycle number for the PCR reaction and the ordinate represents the relative fluorescence of the reaction mixture. It is expected that the reaction mixture will increase in fluorescence as the reaction progresses in the case where the reaction mixture contains cDNA that encodes TCRβ receptors. If no or inappropriate cDNA is found in the mixture, then no increase in fluorescence should be observed. The data in FIG. 1 demonstrate that PCR reactions using TCRCB result in specific increases in fluorescence. The inset to FIG. 1 is a southern blot of the reaction product which further demonstrates that the reaction specifically results in the specific expression of the appropriate DNA. From this type of graph, the cycle threshold may be measured. The cycle threshold (Ct) is defined as the cycle of PCR at which fluorescence of the reaction mixture exceeds the background fluorescence. A lower value for Ct indicates that there is more initial cDNA, thus more message RNA in the cells in vivo.

Further reactions were performed according to the methods described above, wherein the reaction mixtures included the primers found in Table 2. Reactions were performed in 96 well plates. Reaction mixtures in each well were identical except that a single nucleotide primer selected from the group SEQ ID Nos: 33-55 was included in each well. Experiments were performed in triplicate.

Figure 2:
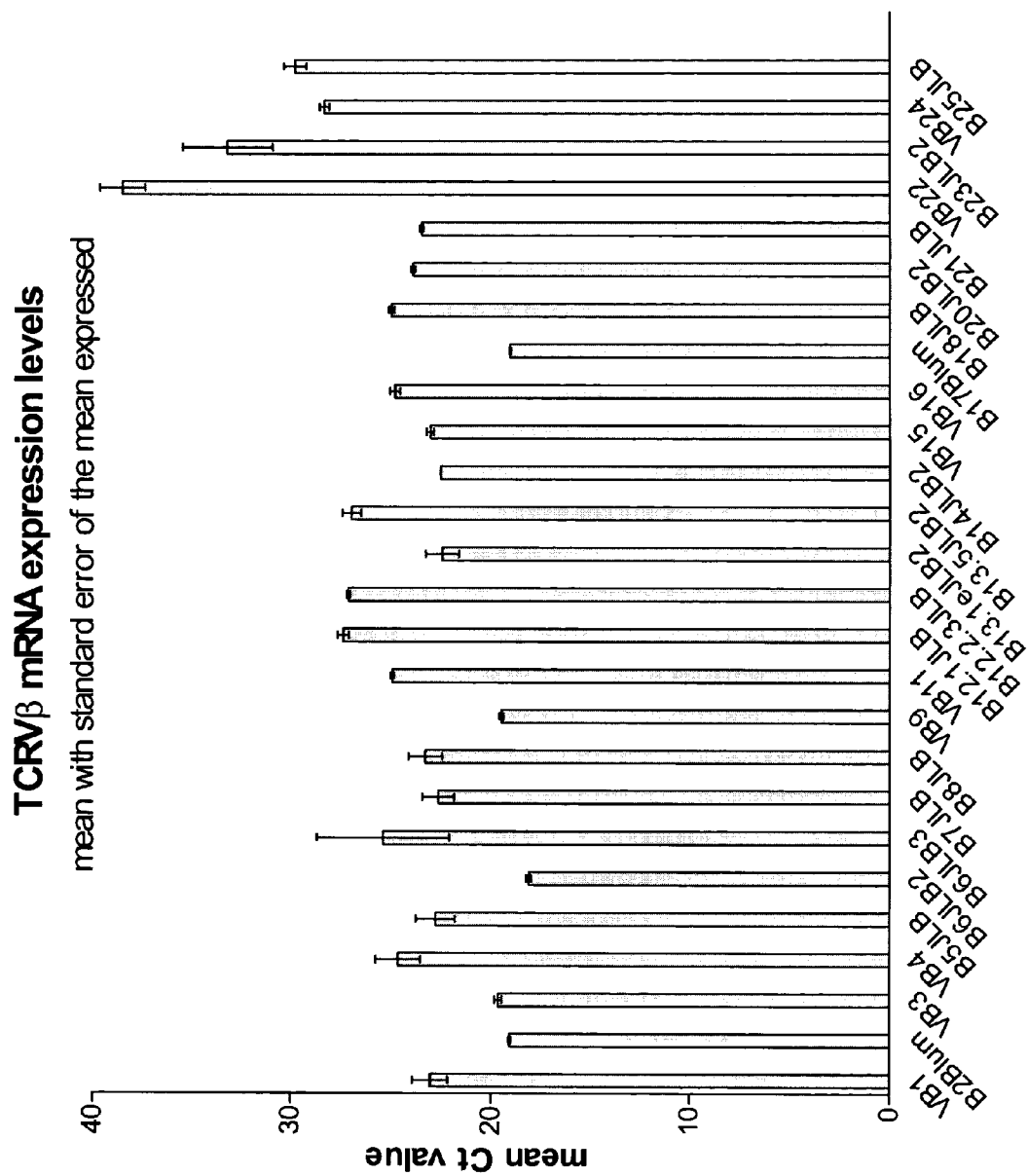
FIG. 2 displays the mRNA expression levels for TCRVβ families in a purified sample of T cells.

During these reactions, the cDNA encoding the members of the TCRVβ family would be amplified specifically. Accordingly, an accurate assessment of the expression of each of the TCRVβ families could be compiled for that patient. The reaction progression was monitored by assessing the fluorescence of the reaction mixture. Data are expressed as the mean Ct value for the three experiments. FIG. 2 displays the results of this analysis. As can be seen, message for the various functional families of TCRVβ were expressed.

Figure 3:
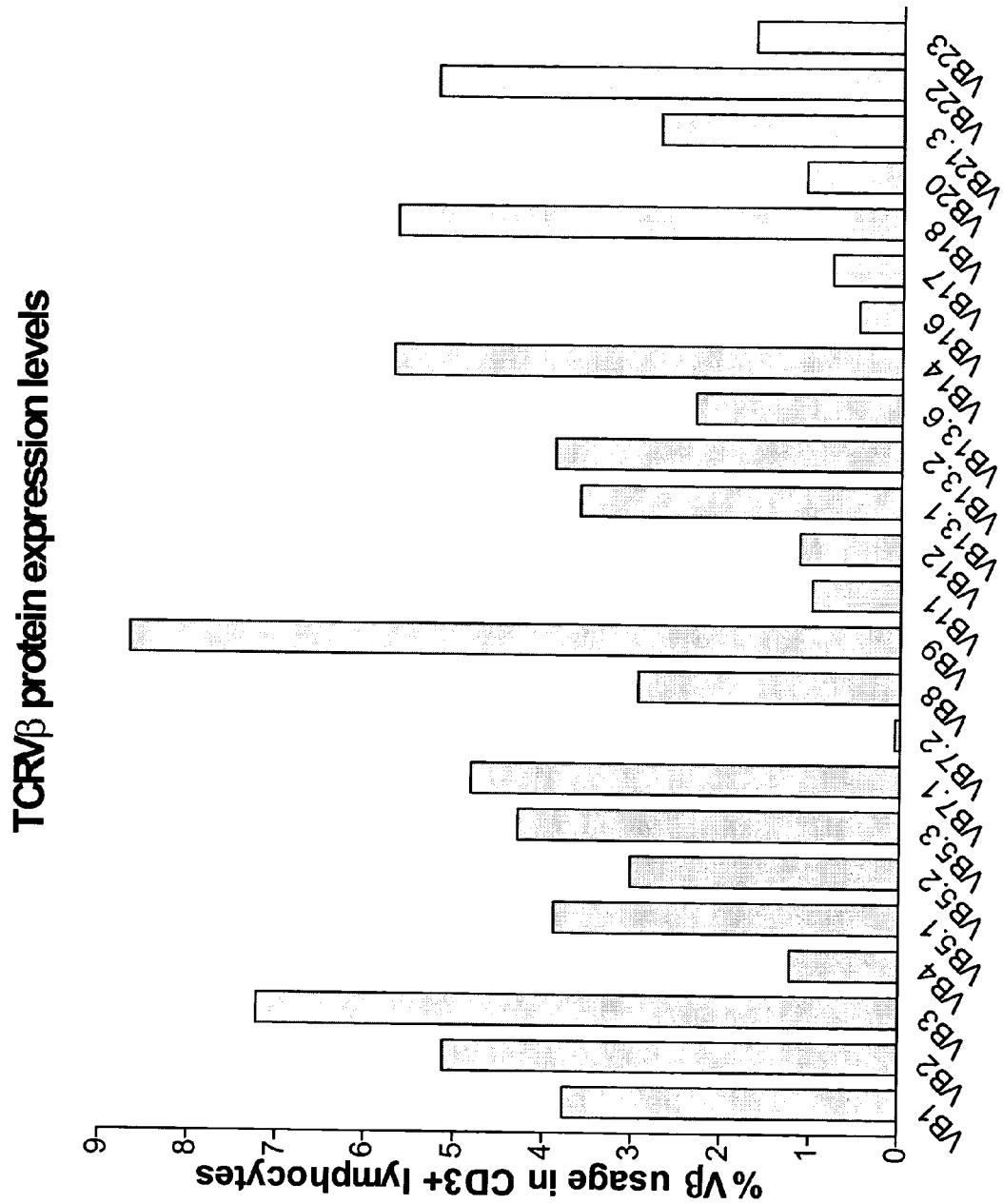
FIG. 3 displays the TCRVβ protein expression levels in a purified fraction of T cells.

The expression of surface TCRVβ protein was assessed through immunohistochemistry. Antibodies are available for the assessment of expression of some of the TCRVβ families. FIG. 3 displays the protein expression levels for the same blood sample that provided the cDNA for the experiments displayed in FIG. 2.

Although the invention has been described in terms of particular embodiments in an application, one of ordinary skill in the art, in light of the teachings herein, can generate additional embodiments and modifications without departing from the spirit of, or exceeding the scope of, the claimed invention. Accordingly, it is understood that the descriptions herein are proffered only to facilitate comprehension of the invention and should not be construed to limit the scope thereof.

What is claimed is:

1. A kit for assessing the expression of T cell receptor variable subunit β in a patient, said kit comprising:
   nucleic acid sequences consisting of SEQ ID Nos: 33-55;
   an enzyme capable of performing a polymerase chain reaction; and
   buffer solutions capable of supporting said polymerase chain reaction.

2. The kit of claim 1, wherein said kit further comprises deoxynucleotide triphosphates.

* * * * *

SEQUENCE LISTING

<160> NUMBER OF SEQ ID NOS: 59

<210> SEQ ID NO 1
<211> LENGTH: 24
<212> TYPE: DNA
<213> ORGANISM: Homo sapiens

<400> SEQUENCE: 1
ggcattaacg gttttgaggc tgga                                    24

<210> SEQ ID NO 2
<211> LENGTH: 21
<212> TYPE: DNA
<213> ORGANISM: Homo sapiens

<400> SEQUENCE: 2
tcagtgttcc agagggagcc a                                       21

<210> SEQ ID NO 3
<211> LENGTH: 24
<212> TYPE: DNA
<213> ORGANISM: Homo sapiens

<400> SEQUENCE: 3
ccgggcagca gacactgctt ctta                                    24

<210> SEQ ID NO 4
<211> LENGTH: 24
<212> TYPE: DNA
<213> ORGANISM: Homo sapiens

<400> SEQUENCE: 4
ttggtatcga cagcttcact ccca                                    24

<210> SEQ ID NO 5
<211> LENGTH: 24
<212> TYPE: DNA
<213> ORGANISM: Homo sapiens

<400> SEQUENCE: 5
cggccaccct gacctgcaac tata                                    24

<210> SEQ ID NO 6
<211> LENGTH: 24
<212> TYPE: DNA
<213> ORGANISM: Homo sapiens

```
<400> SEQUENCE: 6
tccgccaacc ttgtcatctc cgct                                          24

<210> SEQ ID NO 7
<211> LENGTH: 24
<212> TYPE: DNA
<213> ORGANISM: Homo sapiens

<400> SEQUENCE: 7
gcaacatgct ggcggagcac ccac                                          24

<210> SEQ ID NO 8
<211> LENGTH: 22
<212> TYPE: DNA
<213> ORGANISM: Homo sapiens

<400> SEQUENCE: 8
cctgagtgtc caggagggag ac                                            22

<210> SEQ ID NO 9
<211> LENGTH: 24
<212> TYPE: DNA
<213> ORGANISM: Homo sapiens

<400> SEQUENCE: 9
ccagtactcc agacaacgcc tgca                                          24

<210> SEQ ID NO 10
<211> LENGTH: 24
<212> TYPE: DNA
<213> ORGANISM: Homo sapiens

<400> SEQUENCE: 10
ggacagttct ctccacatca ctgc                                          24

<210> SEQ ID NO 11
<211> LENGTH: 21
<212> TYPE: DNA
<213> ORGANISM: Homo sapiens

<400> SEQUENCE: 11
gctgctcatc ctccaggtgg g                                             21

<210> SEQ ID NO 12
<211> LENGTH: 24
<212> TYPE: DNA
<213> ORGANISM: Homo sapiens

<400> SEQUENCE: 12
tcgtcggaac tcttttgatg agca                                          24

<210> SEQ ID NO 13
<211> LENGTH: 24
<212> TYPE: DNA
<213> ORGANISM: Homo sapiens

<400> SEQUENCE: 13
ttcatcaaaa cccttgggga cagc                                          24

<210> SEQ ID NO 14
<211> LENGTH: 24
<212> TYPE: DNA
<213> ORGANISM: Homo sapiens
```

<400> SEQUENCE: 14
cccagcaggc agatgattct cgtt                                      24

<210> SEQ ID NO 15
<211> LENGTH: 24
<212> TYPE: DNA
<213> ORGANISM: Homo sapiens

<400> SEQUENCE: 15
ttgcagacac cgagactggg gact                                      24

<210> SEQ ID NO 16
<211> LENGTH: 24
<212> TYPE: DNA
<213> ORGANISM: Homo sapiens

<400> SEQUENCE: 16
tcaacgttgc tgaagggaat cctc                                      24

<210> SEQ ID NO 17
<211> LENGTH: 24
<212> TYPE: DNA
<213> ORGANISM: Homo sapiens

<400> SEQUENCE: 17
tgggaaaggc cgtgcattat tgat                                      24

<210> SEQ ID NO 18
<211> LENGTH: 24
<212> TYPE: DNA
<213> ORGANISM: Homo sapiens

<400> SEQUENCE: 18
cagcaccaat ttcacctgca gctt                                      24

<210> SEQ ID NO 19
<211> LENGTH: 24
<212> TYPE: DNA
<213> ORGANISM: Homo sapiens

<400> SEQUENCE: 19
acactggctg caacagcatc cagg                                      24

<210> SEQ ID NO 20
<211> LENGTH: 24
<212> TYPE: DNA
<213> ORGANISM: Homo sapiens

<400> SEQUENCE: 20
tccctgttta tccctgccga caga                                      24

<210> SEQ ID NO 21
<211> LENGTH: 24
<212> TYPE: DNA
<213> ORGANISM: Homo sapiens

<400> SEQUENCE: 21
agcaaaattc accatccctg agcg                                      24

<210> SEQ ID NO 22
<211> LENGTH: 24
<212> TYPE: DNA

```
<213> ORGANISM: Homo sapiens

<400> SEQUENCE: 22
cctgaaagcc acgaaggctg atga                                           24

<210> SEQ ID NO 23
<211> LENGTH: 24
<212> TYPE: DNA
<213> ORGANISM: Homo sapiens

<400> SEQUENCE: 23
tgcctcgctg gataaatcat cagg                                           24

<210> SEQ ID NO 24
<211> LENGTH: 24
<212> TYPE: DNA
<213> ORGANISM: Homo sapiens

<400> SEQUENCE: 24
ctggatgcag acacaaagca gagc                                           24

<210> SEQ ID NO 25
<211> LENGTH: 24
<212> TYPE: DNA
<213> ORGANISM: Homo sapiens

<400> SEQUENCE: 25
tggctacggt acaagccgga ccct                                           24

<210> SEQ ID NO 26
<211> LENGTH: 24
<212> TYPE: DNA
<213> ORGANISM: Homo sapiens

<400> SEQUENCE: 26
agcgcagcca tgcaggcatg tacc                                           24

<210> SEQ ID NO 27
<211> LENGTH: 24
<212> TYPE: DNA
<213> ORGANISM: Homo sapiens

<400> SEQUENCE: 27
aagcccgtct cagcaccctc caca                                           24

<210> SEQ ID NO 28
<211> LENGTH: 24
<212> TYPE: DNA
<213> ORGANISM: Homo sapiens

<400> SEQUENCE: 28
tggttgtgca cgagcgagac actg                                           24

<210> SEQ ID NO 29
<211> LENGTH: 24
<212> TYPE: DNA
<213> ORGANISM: Homo sapiens

<400> SEQUENCE: 29
cctgatgata ttactgaagg gtgg                                           24

<210> SEQ ID NO 30
<211> LENGTH: 23
```

```
<212> TYPE: DNA
<213> ORGANISM: Homo sapiens

<400> SEQUENCE: 30
cttcaccctg tattcagctg ggg                                           23

<210> SEQ ID NO 31
<211> LENGTH: 22
<212> TYPE: DNA
<213> ORGANISM: Homo sapiens

<400> SEQUENCE: 31
ggggtaccct acccttttct gg                                            22

<210> SEQ ID NO 32
<211> LENGTH: 23
<212> TYPE: DNA
<213> ORGANISM: Homo sapiens

<400> SEQUENCE: 32
ccagcatgta caagaaggag agg                                           23

<210> SEQ ID NO 33
<211> LENGTH: 24
<212> TYPE: DNA
<213> ORGANISM: Homo sapiens

<400> SEQUENCE: 33
ccgcacaaca gttccctgac ttgc                                          24

<210> SEQ ID NO 34
<211> LENGTH: 22
<212> TYPE: DNA
<213> ORGANISM: Homo sapiens

<400> SEQUENCE: 34
ggccacatac gagcaaggcg tc                                            22

<210> SEQ ID NO 35
<211> LENGTH: 24
<212> TYPE: DNA
<213> ORGANISM: Homo sapiens

<400> SEQUENCE: 35
cgcttctccc ggattctgga gtcc                                          24

<210> SEQ ID NO 36
<211> LENGTH: 24
<212> TYPE: DNA
<213> ORGANISM: Homo sapiens

<400> SEQUENCE: 36
ttcccatcag ccgcccaaac ctaa                                          24

<210> SEQ ID NO 37
<211> LENGTH: 19
<212> TYPE: DNA
<213> ORGANISM: Homo sapiens

<400> SEQUENCE: 37
tgtgtcctgg taccaacag                                                19

<210> SEQ ID NO 38
```

-continued

```
<211> LENGTH: 18
<212> TYPE: DNA
<213> ORGANISM: Homo sapiens

<400> SEQUENCE: 38
cagcgcacag agcagggg                                                       18

<210> SEQ ID NO 39
<211> LENGTH: 22
<212> TYPE: DNA
<213> ORGANISM: Homo sapiens

<400> SEQUENCE: 39
cctgaatgcc ccaacagctc tc                                                  22

<210> SEQ ID NO 40
<211> LENGTH: 21
<212> TYPE: DNA
<213> ORGANISM: Homo sapiens

<400> SEQUENCE: 40
ggtacagaca gaccatgatg c                                                   21

<210> SEQ ID NO 41
<211> LENGTH: 24
<212> TYPE: DNA
<213> ORGANISM: Homo sapiens

<400> SEQUENCE: 41
ttccctggag cttggtgact ctgc                                                24

<210> SEQ ID NO 42
<211> LENGTH: 24
<212> TYPE: DNA
<213> ORGANISM: Homo sapiens

<400> SEQUENCE: 42
tgccaggccc tcacatacct ctca                                                24

<210> SEQ ID NO 43
<211> LENGTH: 22
<212> TYPE: DNA
<213> ORGANISM: Homo sapiens

<400> SEQUENCE: 43
tgtcaccaga ctgagaacca cc                                                  22

<210> SEQ ID NO 44
<211> LENGTH: 25
<212> TYPE: DNA
<213> ORGANISM: Homo sapiens

<400> SEQUENCE: 44
ctgcagtgtg cccaggatat gaacc                                               25

<210> SEQ ID NO 45
<211> LENGTH: 18
<212> TYPE: DNA
<213> ORGANISM: Homo sapiens

<400> SEQUENCE: 45
gagtcgccca gccccaac                                                       18
```

```
<210> SEQ ID NO 46
<211> LENGTH: 24
<212> TYPE: DNA
<213> ORGANISM: Homo sapiens

<400> SEQUENCE: 46
caggcacagg ctaaattctc cctg                                              24

<210> SEQ ID NO 47
<211> LENGTH: 24
<212> TYPE: DNA
<213> ORGANISM: Homo sapiens

<400> SEQUENCE: 47
gcctgcagaa ctggaggatt ctgg                                              24

<210> SEQ ID NO 48
<211> LENGTH: 25
<212> TYPE: DNA
<213> ORGANISM: Homo sapiens

<400> SEQUENCE: 48
gaaaggagat atagctgaag ggtac                                             25

<210> SEQ ID NO 49
<211> LENGTH: 22
<212> TYPE: DNA
<213> ORGANISM: Homo sapiens

<400> SEQUENCE: 49
gatgagtcag gaatgccaaa gg                                                22

<210> SEQ ID NO 50
<211> LENGTH: 23
<212> TYPE: DNA
<213> ORGANISM: Homo sapiens

<400> SEQUENCE: 50
ctggcttcta tctctgtgcc tgg                                               23

<210> SEQ ID NO 51
<211> LENGTH: 22
<212> TYPE: DNA
<213> ORGANISM: Homo sapiens

<400> SEQUENCE: 51
ccactctcaa gatccagcct gc                                                22

<210> SEQ ID NO 52
<211> LENGTH: 24
<212> TYPE: DNA
<213> ORGANISM: Homo sapiens

<400> SEQUENCE: 52
aagtgatctt gcgctgtgtc ccca                                              24

<210> SEQ ID NO 53
<211> LENGTH: 18
<212> TYPE: DNA
<213> ORGANISM: Homo sapiens

<400> SEQUENCE: 53
cagggtccag gtcaggac                                                     18
```

```
<210> SEQ ID NO 54
<211> LENGTH: 24
<212> TYPE: DNA
<213> ORGANISM: Homo sapiens

<400> SEQUENCE: 54
cccagtttgg aaagccagtg accc                                          24

<210> SEQ ID NO 55
<211> LENGTH: 23
<212> TYPE: DNA
<213> ORGANISM: Homo sapiens

<400> SEQUENCE: 55
gaaacaggta tgcccaagga aag                                           23

<210> SEQ ID NO 56
<211> LENGTH: 32
<212> TYPE: DNA
<213> ORGANISM: Homo sapiens
<220> FEATURE:
<221> NAME/KEY: misc_feature
<222> LOCATION: (1)..(1)
<223> OTHER INFORMATION: 5' 6-FAM "fluorescence emitting molecule"
<220> FEATURE:
<221> NAME/KEY: misc_feature
<222> LOCATION: (32)..(32)
<223> OTHER INFORMATION: 3' BHQ-1 "fluorescence quenching molecule"

<400> SEQUENCE: 56
cctaccgatc ctgctcctcc tggcacagga tc                                 32

<210> SEQ ID NO 57
<211> LENGTH: 32
<212> TYPE: DNA
<213> ORGANISM: Homo sapiens
<220> FEATURE:
<221> NAME/KEY: misc_feature
<222> LOCATION: (32)..(32)
<223> OTHER INFORMATION: 3' BHQ-1 "fluorescence quenching molecule"
<220> FEATURE:
<221> NAME/KEY: misc_feature
<222> LOCATION: (1)..(1)
<223> OTHER INFORMATION: 5' 6-FAM "fluorescence emitting molecule"

<400> SEQUENCE: 57
tctgtgctga ccccactgtg cacctccttc cc                                 32

<210> SEQ ID NO 58
<211> LENGTH: 23
<212> TYPE: DNA
<213> ORGANISM: Homo sapiens

<400> SEQUENCE: 58
ccagatgtgt aaggctgtgg atc                                           23

<210> SEQ ID NO 59
<211> LENGTH: 20
<212> TYPE: DNA
<213> ORGANISM: Homo sapiens

<400> SEQUENCE: 59
gctgctcctt gaggggctgc                                               20
```